US012605703B1

(12) United States Patent
McKinzy, Sr.

(10) Patent No.: US 12,605,703 B1
(45) Date of Patent: Apr. 21, 2026

(54) BINARY LOGIC-BASED BLOOD TYPING KIT

(71) Applicant: Michael E. McKinzy, Sr., Trustee of the Michael McKinzy Trust, Overland Park, KS (US)

(72) Inventor: Michael Eugene McKinzy, Sr., Overland Park, KS (US)

(73) Assignee: Michael E. McKinzy, Sr., trustee of the Michael McKinzy Trust dated Apr. 16, 2018, Overland Park, KS (US)

( * ) Notice: Subject to any disclaimer, the term of this patent is extended or adjusted under 35 U.S.C. 154(b) by 0 days.

(21) Appl. No.: 19/216,473

(22) Filed: May 22, 2025

(51) Int. Cl.
B01L 3/00 (2006.01)
G01N 33/80 (2006.01)

(52) U.S. Cl.
CPC .............. B01L 3/502 (2013.01); G01N 33/80 (2013.01); B01L 2200/028 (2013.01); B01L 2200/0689 (2013.01); B01L 2200/16 (2013.01); B01L 2300/027 (2013.01); B01L 2300/0816 (2013.01); B01L 2300/0864 (2013.01)

(58) Field of Classification Search
CPC .............. B01L 3/502; B01L 2200/028; B01L 2200/0689; B01L 2200/16; B01L 2300/027; B01L 2300/0816; B01L 2300/0864; G01N 33/80
See application file for complete search history.

(56) References Cited

U.S. PATENT DOCUMENTS

2004/0152208 A1* 8/2004 Hutchinson .......... G01N 33/523
702/19
2008/0138890 A1* 6/2008 Horiike ................ G01N 33/491
435/288.7

(Continued)

FOREIGN PATENT DOCUMENTS

CN 1525174 A 9/2004
CN 202776581 U 3/2013
(Continued)

*Primary Examiner* — Dennis White
(74) *Attorney, Agent, or Firm* — John Rizvi; John Rizvi, P.A.—The Patent Professor®

(57) ABSTRACT

A disposable blood typing device is provided for determining ABO and RhD blood types using binary logic-based interpretation. The device includes a sample application area, test zones containing dried anti-A, anti-B, and optionally anti-D reagents, and a result output mechanism configured to display a binary outcome for each antigen. Binary values are assigned based on visible agglutination reactions, which are processed through a logical mapping structure—such as a printed chart, mechanical indicator, or electronic logic circuit—to determine the corresponding blood type. The device may incorporate visual indicators, control regions, waste containment, and optional digital components for electronic display or wireless data transmission. Designed for single use, the system facilitates self-administered or point-of-care testing without requiring clinical expertise, and may be integrated with mobile applications or health records systems. The invention enhances test accuracy, usability, and data interoperability while minimizing contamination risk and interpretation error.

20 Claims, 10 Drawing Sheets

(56)                References Cited

U.S. PATENT DOCUMENTS

| | | | | |
|---|---|---|---|---|
| 2016/0025640 A1* | 1/2016 | Wu | ...................... | A61B 5/1455 |
| | | | | 422/403 |
| 2020/0363434 A1* | 11/2020 | Buffiere | ............ | B01L 3/502776 |
| 2024/0157356 A1* | 5/2024 | Xu | ...................... | B01L 3/50273 |

FOREIGN PATENT DOCUMENTS

| | | | |
|---|---|---|---|
| CN | 111218396 A | 6/2020 |
| EP | 2315024 A4 | 7/2011 |
| EP | 3711669 A1 | 8/2021 |
| JP | 2009030997 A | 2/2009 |

* cited by examiner

| | A | B | AB | OUTPUT 1 | OUTPUT 2 |
|---|---|---|---|---|---|
| 1 | 1 | 0 | 0 | 1 | 1 |
| 2 | 0 | 0 | 1 | 1 | 1 |
| 3 | 0 | 1 | 0 | 0 | 0 |
| 4 | 0 | 1 | 1 | 1 | 0 |
| 5 | 1 | 0 | 0 | 0 | 0 |
| 6 | 1 | 0 | 1 | 0 | 0 |
| 7 | 1 | 1 | 0 | 0 | 1 |
| 8 | 1 | 1 | 1 | 0 | 0 |

| | | | POSITIVE | NEGATIVE |
|---|---|---|---|---|
| A | 1 | | | NEGATIVE 1 |
| A | 1 | | POSITIVE 1 | |
| B | | 1 | | NEGATIVE 1 |
| B | | 1 | POSITIVE 1 | |
| AB | 1 | 1 | | NEGATIVE 1 |
| AB | 1 | 1 | POSITIVE 1 | |
| O | | | | NEGATIVE 1 |
| O | | | POSITIVE 1 | |

FIG. 9

BINARY LOGIC-BASED BLOOD TYPING KIT

FIELD OF THE INVENTION

The present invention relates generally to medical diagnostic devices and, more particularly, to disposable, at-home blood type testing kits. Specifically, the invention pertains to a binary logic-based detection and identification system that determines the ABO blood type and RhD factor of a blood sample using colorimetric reagents, logical mapping algorithms, and optionally electronic integration for visual or digital output.

BACKGROUND OF THE INVENTION

The determination of an individual's blood type is an essential diagnostic procedure that serves as a cornerstone in numerous clinical and emergency medical scenarios. Blood typing plays a critical role in ensuring compatibility for blood transfusions, organ transplants, and hematological evaluations. The most clinically significant blood group systems are the ABO and Rh(Rhesus) systems. The ABO system classifies blood into four main groups—A, B, AB, and O—based on the presence or absence of antigens on the surface of red blood cells. The Rh system, primarily concerned with the D antigen, further categorizes each ABO group as either Rh-positive or Rh-negative. In total, this classification yields eight standard blood types: A+, A−, B+, B−, AB+, AB−, O+, and O−. Accurate typing of these blood groups is critical because incompatibility during transfusion or transplantation can result in immune reactions that are potentially fatal.

Historically, blood type determination has relied on serological testing techniques developed over the course of the 20th century. These methods utilize antigen-antibody interactions to reveal the presence or absence of specific antigens on red blood cells. Forward typing involves mixing a patient's red blood cells with known antisera (e.g., anti-A and anti-B) to detect agglutination reactions, indicating the presence of corresponding antigens. Reverse typing, conversely, mixes patient plasma with reagent red cells to identify antibodies in the plasma. Rh typing generally follows a similar protocol, employing anti-D reagent to test for the presence of the D antigen.

Most blood typing in clinical settings is performed using either manual slide or tube agglutination methods or semi-automated platforms employing column agglutination or microplate-based assays. Gel card technologies and flow cytometry-based assays have also been developed to enhance accuracy and reduce the subjectivity of visual interpretation. While these laboratory-based systems are well-established and provide reliable results under controlled conditions, they remain largely inaccessible to individuals outside of clinical environments.

Several point-of-care testing (POCT) kits have emerged to fill this accessibility gap. These include manually operable blood typing cards and test strips that incorporate dried reagents and colorimetric indicators. While these systems represent a move toward decentralization of diagnostic testing, they often still require some degree of expertise for correct operation and interpretation. Moreover, such kits typically necessitate controlled environmental conditions and are prone to error due to visual subjectivity or reagent degradation over time. Many rely on agglutination patterns visible to the naked eye, which may be difficult to interpret for individuals without medical training or under non-ideal lighting conditions. This creates a barrier to truly independent use by laypersons in home, field, or emergency settings.

Existing commercial solutions that facilitate at-home blood testing often focus on broader health metrics such as glucose levels, cholesterol, or infectious disease markers. When it comes to blood typing, however, the market remains limited. Some experimental devices have attempted to incorporate microfluidics and lateral flow principles to streamline the testing process, but these remain largely in research phases or limited deployment. Although certain patents have disclosed systems combining multiple wells with specific antibodies dried into solid phases for serological reactions, these systems still depend on traditional interpretations of physical agglutination reactions and manual input/output without offering an intuitive or binary logic-based user experience.

Another area of technological development involves the use of digital components to enhance diagnostics. Some recent devices include light sensors, LEDs, or image recognition software to detect and quantify agglutination reactions more objectively. However, these technologies often introduce higher costs, power requirements, and system complexity, which are contrary to the goal of creating simple, disposable, and low-cost test kits for broad public distribution. Furthermore, integration with mobile or computing platforms remains inconsistent, and there is often no standardized means of converting biological reactions into digital outputs that can be interpreted programmatically or stored for electronic medical records.

Despite decades of advancement in diagnostic devices, there remain persistent challenges associated with implementing an ideal blood typing solution suitable for home or remote use. One fundamental drawback of current systems is the lack of integration between the biological detection mechanism and an intuitive, logic-based interpretation interface. Traditional test kits rely on analog outcomes—visible clumping or color changes—which must be interpreted based on context, user perception, and testing environment. This introduces the potential for misinterpretation, especially among non-professional users, and leads to the risk of erroneous self-diagnosis or incorrect medical assumptions.

In addition, existing solutions typically do not feature mechanisms for binary or algorithmic processing of the results. That is, while they may show whether anti-A or anti-B reagents yield a reaction, they do not frame these reactions within a defined logical or computational model that can systematize the diagnostic decision-making. The lack of binary logic, Boolean frameworks, or truth table-based structures in these systems limits their compatibility with modern digital health technologies. There is a growing demand for medical diagnostic devices that not only provide accurate biological readings but also facilitate digital integration for data capture, analysis, and sharing.

The majority of traditional blood typing kits are also reusable or semi-reusable, which introduces another set of complications. Reusability can lead to cross-contamination between tests if not properly managed, particularly in field or home settings where sterile technique cannot be guaranteed. Moreover, the requirement for cleanup, maintenance, and calibration reduces convenience and deters regular use by the general public. Even among disposable kits, cost remains a barrier due to the inclusion of glass or rigid plastic components, the need for multiple reagent chambers, or reliance on refrigerated reagents.

Another key limitation in existing blood typing technologies is the constrained antigen scope. Some consumer-grade tests focus only on the ABO system, neglecting the Rh factor, which is essential for clinical safety. Others fail to account for variant antigen expressions, such as weak D or partial D types, which can yield false negatives or ambiguous results. These variants are clinically significant in specific populations, such as pregnant women or individuals requiring repeated transfusions. While high-precision laboratory tests can detect these variants using extended protocols and confirmatory testing, most point-of-care and home-use devices are not equipped to do so, thus limiting their diagnostic comprehensiveness.

Moreover, current systems often lack scalability and adaptability. Most existing kits are rigid in form and purpose—they are designed to determine a fixed set of parameters without the potential for expansion or customization. This rigidity limits their application in environments that might benefit from additional features, such as data logging, user authentication, or multi-analyte testing capabilities. As a result, they fail to fully leverage modern electronics, informatics, and miniaturization techniques that have revolutionized other sectors of diagnostics.

The desired improvements in this space include, but are not limited to, enhanced portability, intuitive interpretation, digital integration, contamination resistance, and logical simplification of the output process. An ideal blood typing solution would be lightweight, compact, and fully disposable, utilizing widely available manufacturing materials to minimize cost. The system should be operable by untrained individuals in non-clinical environments without compromising accuracy. Visual or digital outputs must be easy to interpret and devoid of ambiguity, preferably framed in a binary or algorithmic logic system to support interoperability with health informatics platforms.

Additionally, such a system should minimize biological exposure risk and biohazard potential by ensuring containment of all fluids and reagents within a sealed housing. The use of single-use, self-contained cassettes would alleviate cross-contamination concerns and eliminate the need for disinfection or maintenance. Furthermore, the test process should not require ancillary equipment such as centrifuges, pipettes, or microscopes, and it should operate reliably across a range of environmental conditions without the need for calibration or training.

To support integration with the broader ecosystem of digital health tools, the ideal diagnostic kit should offer optional or embedded digital capabilities. These could include visual indicators such as LEDs, programmable displays, or Bluetooth-enabled interfaces that convert biological data into electronic outputs for mobile devices or cloud storage. Moreover, such a system should adopt standardized data formats or logical schemas to ensure compatibility with electronic health records (EHRs), telemedicine applications, and remote diagnostics platforms.

In sum, the current state of the art in blood type determination suffers from several limitations, including reliance on subjective visual interpretation, requirement for clinical infrastructure, susceptibility to contamination, high cost of production, and lack of logical or digital output processing. There is an unmet need for a simplified, self-contained, and logic-based blood typing system that is tailored for use by the general public, suitable for mass deployment, and capable of producing results that are unambiguous, reliable, and compatible with digital workflows.

Such improvements would not only expand access to life-saving information in underserved or resource-limited settings but would also contribute to the evolution of personalized medicine, remote care, and emergency preparedness. In today's healthcare landscape—where rapid, decentralized diagnostics are increasingly vital—innovations that address these shortcomings would represent a significant advancement over the current state of the art.

SUMMARY OF THE INVENTION

The present invention is directed to a disposable blood type testing kit configured to identify an individual's ABO and RhD blood group through a simplified logic-based detection mechanism. The kit utilizes conventional serological reagents—such as anti-A, anti-B, and anti-D antibodies—combined with a binary output logic structure that assigns digital values (e.g., "1" for positive reaction, "0" for negative reaction) to the results of antigen-antibody interactions. These binary results are processed according to a pre-established Boolean truth table or logical algorithm, yielding a clear blood type classification (e.g., A+, B−, AB+, O−). The device may be formed as a single-use, self-contained cassette resembling a lateral flow or pregnancy test, optionally equipped with features such as LED indicators or passive colorimetric windows to visually display the binary results and/or blood type outcome. In some embodiments, the kit may include data encoding or electronic transmission capabilities for integration with health monitoring systems.

Unlike conventional blood typing systems that rely on agglutination patterns requiring expert interpretation, the present invention introduces a logic-driven architecture that standardizes test results into binary values, thereby eliminating ambiguity and minimizing user error. The system is fully disposable, reducing the risk of cross-contamination and biohazard exposure, and is designed for ease of use by non-professional individuals without the need for laboratory equipment or specialized training. Compared to prior solutions that may involve multiple wells, external readers, or partially reusable components, the disclosed invention offers a low-cost, compact alternative suitable for widespread distribution and deployment in home, field, or emergency settings. Its digital or logic-based framework also allows for integration with mobile applications, electronic medical records, or telehealth platforms-capabilities not present in traditional analog blood typing kits-thereby providing a modern, scalable solution to meet evolving diagnostic and public health needs.

In a first implementation of the invention, a disposable blood typing device for determining an ABO and RhD blood type of a blood sample, comprises:

(a) a housing comprising a plurality of test zones including (i) a first test zone containing an anti-A reagent configured to detect an A antigen in the blood sample, (ii) a second test zone containing an anti-B reagent configured to detect a B antigen in the blood sample, and (iii) a third test zone containing an anti-D reagent configured to detect a D antigen in the blood sample;

(b) a sample application area in fluid communication with each of the plurality of test zones;

(c) a result output mechanism associated with each test zone and configured to display a binary output comprising a first state indicating presence of antigen and a second state indicating absence of antigen; and (d) a logical mapping structure operatively associated with the result output mechanism and configured to associate the combination of binary outputs from the first, second, and third test zones with a specific ABO and RhD blood type classification.

In a second aspect, the result output mechanism may comprise a colorimetric indicator configured to change color in response to an agglutination reaction in each respective test zone.

In another aspect, the result output mechanism may comprise an electronic indicator selected from the group consisting of a light-emitting diode (LED), a digital display, or a visual signal on a screen.

In another aspect, each test zone may be operatively coupled to a corresponding LED that illuminates in a first color in response to a positive reaction and in a second color in response to a negative reaction.

In another aspect, the logical mapping structure may comprise a preconfigured Boolean logic circuit that receives the binary outputs from the test zones and generates an output signal corresponding to the determined blood type.

In another aspect, the logical mapping structure may comprise a printed chart or matrix on the housing that maps all possible binary combinations to corresponding blood type classifications.

In another aspect, the device may comprise a display area on the housing configured to visually present the determined blood type to a user based on the binary outputs of the test zones.

In another aspect, each of the anti-A reagent, anti-B reagent, and anti-D reagent may be provided in a dried, stabilized form within a gel or porous membrane.

In another aspect, the sample application area may be configured to receive a whole blood sample and direct the sample to the test zones via capillary action or microfluidic channels.

In another aspect, the housing may be formed as a single-use, sealed cassette configured to prevent re-use or cross-contamination.

In another aspect, the device may further comprise a waste containment region within the housing configured to retain excess sample and reduce biological exposure risk.

In another aspect, the logical mapping structure may comprise an integrated circuit configured to convert the binary outputs into a machine-readable data format.

In another aspect, the device may further comprise a communication module configured to transmit the machine-readable data to an external device such as a smartphone, a computer, or a remote server.

In another aspect, the device may further comprise a control region containing a control reagent configured to confirm sample validity and reagent functionality.

In another aspect, the device may further comprise a power source configured to energize one or more components of the result output mechanism or logical mapping structure.

In another aspect, the result output mechanism may comprise a mechanical window revealing a graphical symbol corresponding to the result of each test zone.

In another aspect, the housing may comprise instructional markings indicating sample placement, test zone identification, and interpretation instructions.

In another aspect, the logical mapping structure may be configured to generate a unique output code representative of the blood type, wherein the output code may be scannable or interpretable by an external reader device.

In another implementation of the invention, a disposable blood typing device for determining an ABO and RhD blood type of a blood sample, comprises:

(a) a sealed housing formed as a single-use cassette, the housing comprising a sample application area and a plurality of fluidically connected test zones;

(b) a first test zone containing a dried anti-A reagent configured to detect an A antigen in the blood sample;

(c) a second test zone containing a dried anti-B reagent configured to detect a B antigen in the blood sample;

(d) a third test zone containing a dried anti-D reagent configured to detect a D antigen in the blood sample;

(e) a visual output mechanism associated with each test zone, the visual output mechanism comprising colorimetric indicators configured to change color in response to an agglutination reaction;

(f) a printed mapping region disposed on the housing, the printed mapping region comprising a binary logic chart that maps combinations of agglutination results in the test zones to specific ABO and RhD blood types;

(g) a control region comprising a control reagent configured to indicate validity of the test; and (h) a waste containment area positioned downstream of the test zones and configured to collect excess sample material.

In another implementation of the invention, a method for determining an ABO and RhD blood type of a blood sample using a disposable blood typing device, the method comprising:

(a) providing a disposable blood typing device comprising:

(i) a sample application area, (ii) a first test zone comprising a dried anti-A reagent, (iii) a second test zone comprising a dried anti-B reagent, (iv) a third test zone comprising a dried anti-D reagent, and (v) a result output mechanism configured to display a visual indication of agglutination;

(b) applying a blood sample to the sample application area;

(c) allowing the blood sample to flow to each of the first, second, and third test zones;

(d) observing the result output mechanism at each test zone to determine whether agglutination has occurred;

(e) assigning a binary value to each test zone based on whether agglutination is observed, wherein agglutination corresponds to a first binary value and absence of agglutination corresponds to a second binary value; and (f) referencing a predefined binary mapping chart to determine a corresponding ABO and RhD blood type classification based on the assigned binary values.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which:

FIG. 3 presents a tabular mapping of input values and corresponding binary logic outputs for various antigen reactions, illustrating the algorithmic basis for determining blood type classification from sample results;

FIG. 9 presents a tabular chart illustrating ABO and Rh(D) blood type classifications based on binary input values, showing combinations of A and B antigen detection and corresponding Rh(D) positive or negative indicators for determining blood types A, B, AB, and O with Rh factor status.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The present disclosure relates to a disposable blood typing device 100 configured to determine a blood type classification based on antigen detection and logical mapping. The blood typing device 100 may include chemical reagents, a result interpretation mechanism, and a logical framework configured to represent biological reactions as binary values. The device 100 may be applied in home, clinical, or mobile environments to determine ABO and RhD blood types based on a user-supplied blood sample. The system may utilize standard serological principles in combination with a logic-based framework to generate clear and unambiguous outputs. The implementation of a logic-based framework may reduce reliance on user interpretation and promote diagnostic confidence. The device 100 may be manufactured in a compact format for single use and rapid deployment in field or decentralized settings.

Figure 1:
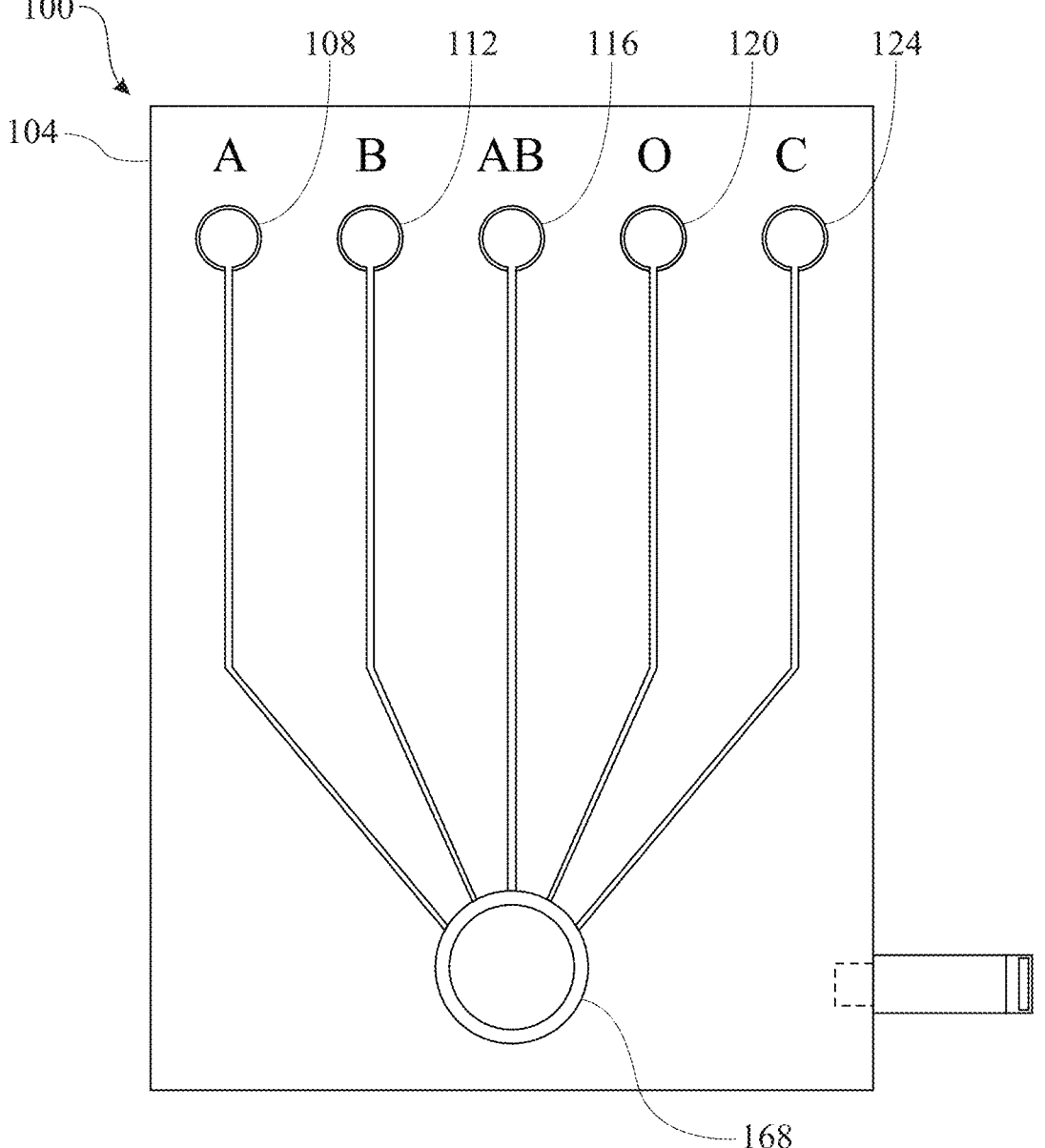
FIG. 1 presents a diagrammatic representation of a front-facing layout for identifying ABO blood types using labeled zones A, B, AB, O, and C, in accordance with an illustrative embodiment of the invention.

Referring now to FIG. 1, an exemplary representation of a front-facing layout of a blood typing test interface 104 is shown. The interface 104 may include distinct zones labeled A 108, B 112, AB 116, O 120, and C 124. These zones may correspond to discrete areas pre-treated with blood typing reagents, such as monoclonal anti-A, anti-B, or control indicators. Each of the regions A 108 and B 112 may be configured to receive a sample and initiate a reaction with anti-A and anti-B reagents respectively. Region AB 116 may serve as an interpretive indicator correlating to the presence of both antigens, while region O 120 may indicate the absence of both A and B antigens. Control region C 124 may be treated with a control reagent to confirm flow adequacy and overall reagent functionality during the testing process.

Figure 2:
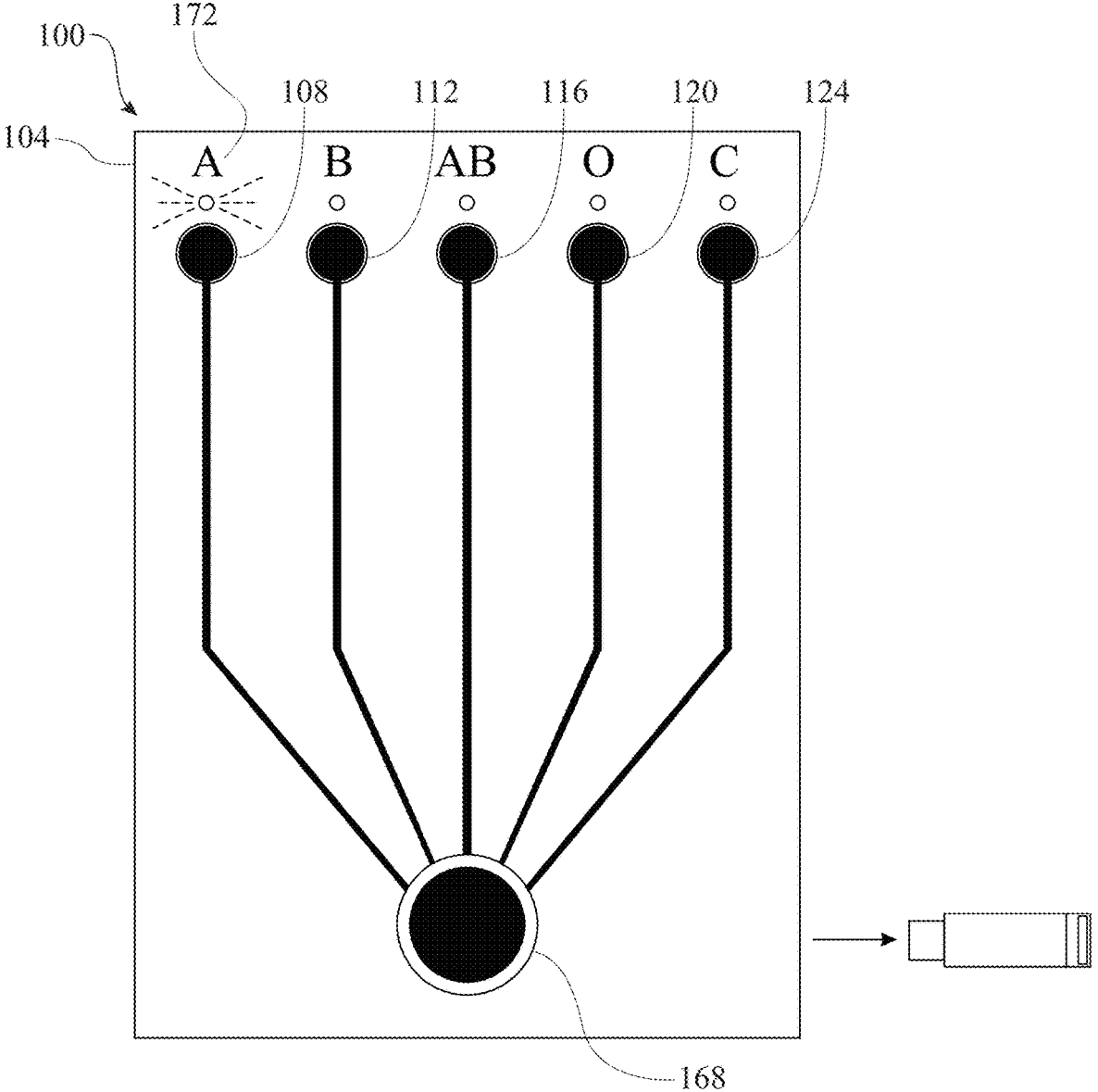
FIG. 2 presents a similar diagrammatic layout to that shown in FIG. 1, illustrating potential positioning of test result zones used for blood typing classification

In FIG. 2, an alternate view of the layout 104 is depicted, with similar zones A 108, B 112, AB 116, O 120, and C 124 arranged in a pattern allowing clear visual separation of each reaction site. This alternate orientation may be designed to reduce test overlap or cross-reaction by spacing the zones apart, thereby enabling easier interpretation by eye or sensor. The arrangement may also facilitate automated detection by optical systems capable of reading and interpreting changes in reflectivity, opacity, or color. Use of spatially isolated zones may assist in ensuring distinct signal resolution, especially when evaluating faint agglutination reactions. In some implementations, light-emitting diodes or embedded fiber optic channels may be used to enhance visualization of positive or negative reactions in these zones. Such integrated lighting components may improve low-light usability and increase the reliability of home-based diagnostics.

Referring now to FIG. 3, a logic table diagram 128 is provided. The logic table diagram 128 shows a sequence of input conditions and the corresponding binary outputs that may be generated from the antigen testing process. Sample identifiers 132 may represent patient blood types or hypothetical examples. Binary values 136 associated with each test condition may correspond to antigen presence (1) or absence (0). These values may be fed into a truth table that determines which blood type is present. Output fields 140 may display final results derived from the input combinations, allowing a user or microcontroller to determine ABO and RhD classifications. Each row in the logic table may represent a different outcome path and may be programmed into a digital microprocessor or referenced from a printed chart.

The binary outputs from the sample testing procedure may be used to populate an output table 140 within the logic diagram 128. The logic operations may follow a predefined algorithm that evaluates combinations of the individual antigen results. For example, if anti-A produces a positive reaction (1) and anti-B produces a negative reaction (0), the resulting blood type may be classified as A. If both anti-A and anti-B produce positive reactions (1, 1), the sample may be classified as AB. If both produce negative reactions (0, 0), the sample may be classified as O. If anti-A is 0 and anti-B is 1, the classification may be B. RhD typing may further distinguish each result into positive or negative subtypes depending on reactivity within the D antigen zone.

Figure 4:
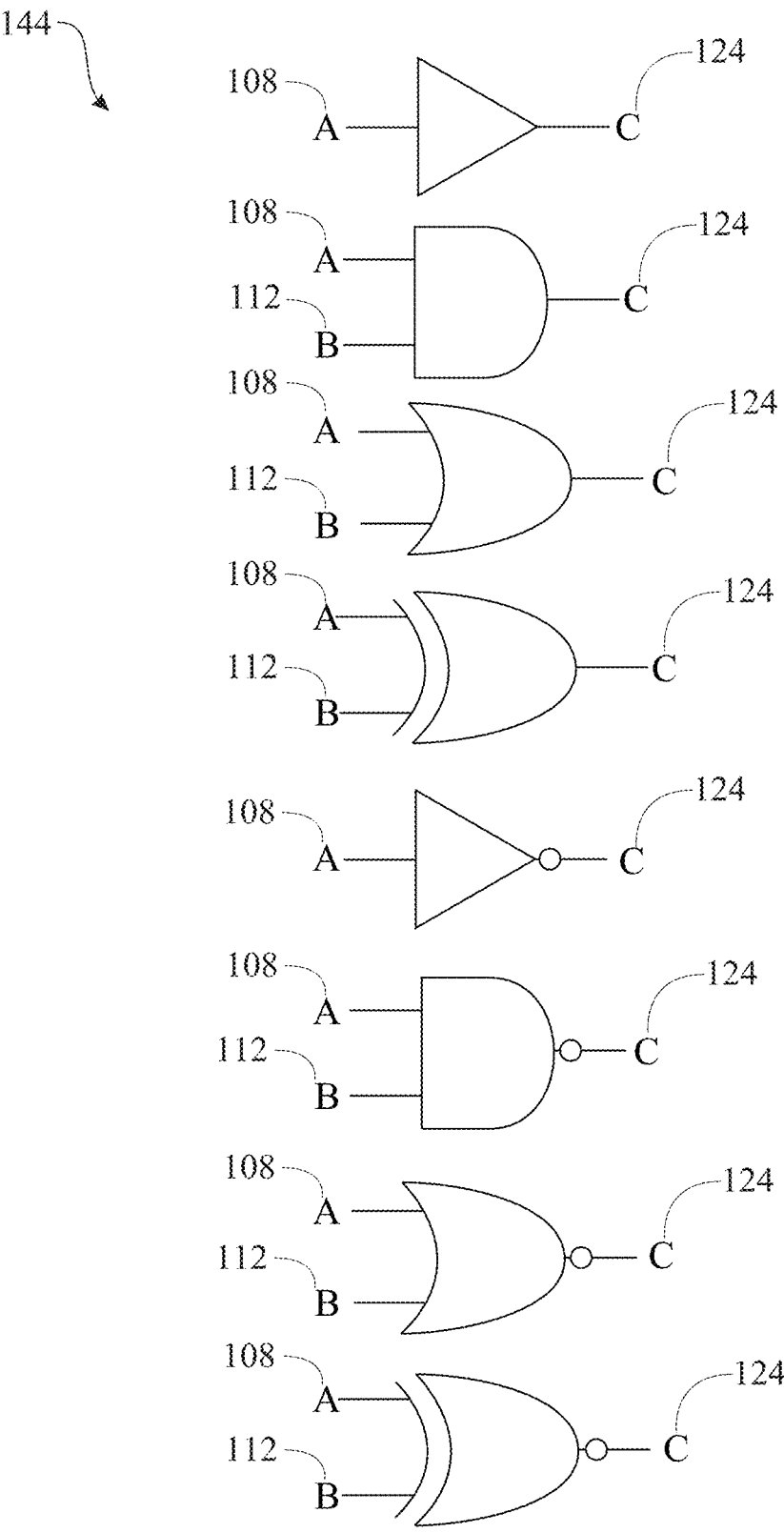
FIG. 4 presents a visual layout diagram illustrating repeated antigen-specific detection zones, including groupings of zones labeled A, B, and C, used to visually convey detection logic across a disposable test strip or surface.

Referring now to FIG. 4, a repetition-based layout diagram 144 is presented. The diagram 144 may include multiple replicated antigen detection zones such as a series of A zones 108, B zones 112, and control zones C 124. This repeated pattern may allow for multiple parallel tests to be conducted on a single strip, either to verify results or support batch testing. Each zone may operate independently to validate antigen presence or absence using identical reagents. Redundant data from replicated zones may be used for averaging, or to trigger a fault tolerance threshold if inconsistent results arise. The layout may also permit real-time quality control analysis where inconsistent or faint results can be interpreted in aggregate. Use of repeated elements may support diagnostic confidence and improve overall test accuracy.

The structure shown in FIG. 4 may also support mechanical or optical scanning. The layout 144 may be designed to interface with an electronic or optical reader that detects colorimetric or fluorescence-based changes corresponding to antigen-antibody reactions. Each positive reaction in a zone A 108 or B 112 may alter the color or reflectivity of the region, which may be detected by an image sensor and translated into a binary value. Sensors embedded within or adjacent to each test zone may detect a signal threshold indicating a positive or negative result. Results may then be compiled digitally or conveyed through a passive output system such as a moving dial, label window, or printed matrix. Use of automation-compatible geometry may make the system adaptable for hospital-grade electronic readers or mobile health applications.

Figure 5:
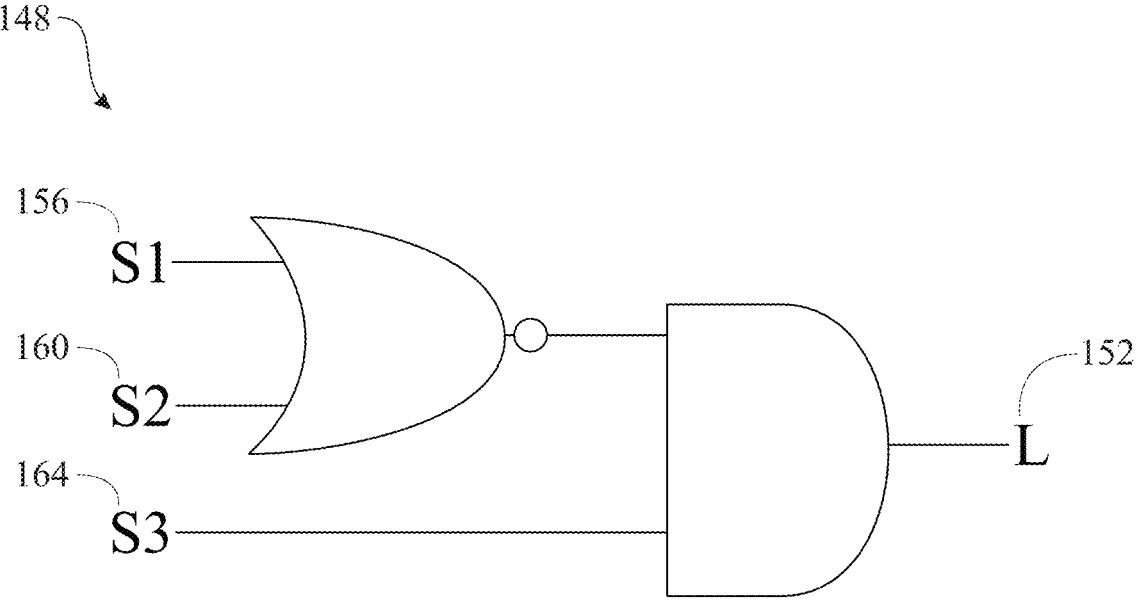
FIG. 5 presents a schematic representation of a circuit or logical control system labeled with L, S1, S2, and S3, which may correspond to system logic, signal processing elements, or result interpretation mechanisms integrated within the blood typing device.

In FIG. 5, a schematic logic diagram 148 is shown, which may represent an abstracted version of the logical decision framework used in the device 100. Logic gates or nodes labeled L 152, S1 156, S2 160, and S3 164 may represent input signal pathways, decision points, or electronic modules. These elements may be physical circuits, software functions, or graphical representations of logic pathways implemented by a microcontroller. The logic gates may correspond to AND, OR, NOT, XOR, or other standard Boolean functions. The L node 152 may act as the logic core aggregating binary values from each test zone and producing a final resolved blood type classification. Outputs from the logic diagram 148 may drive displays, initiate wireless signals, or store results in memory for retrieval.

Figure 6:
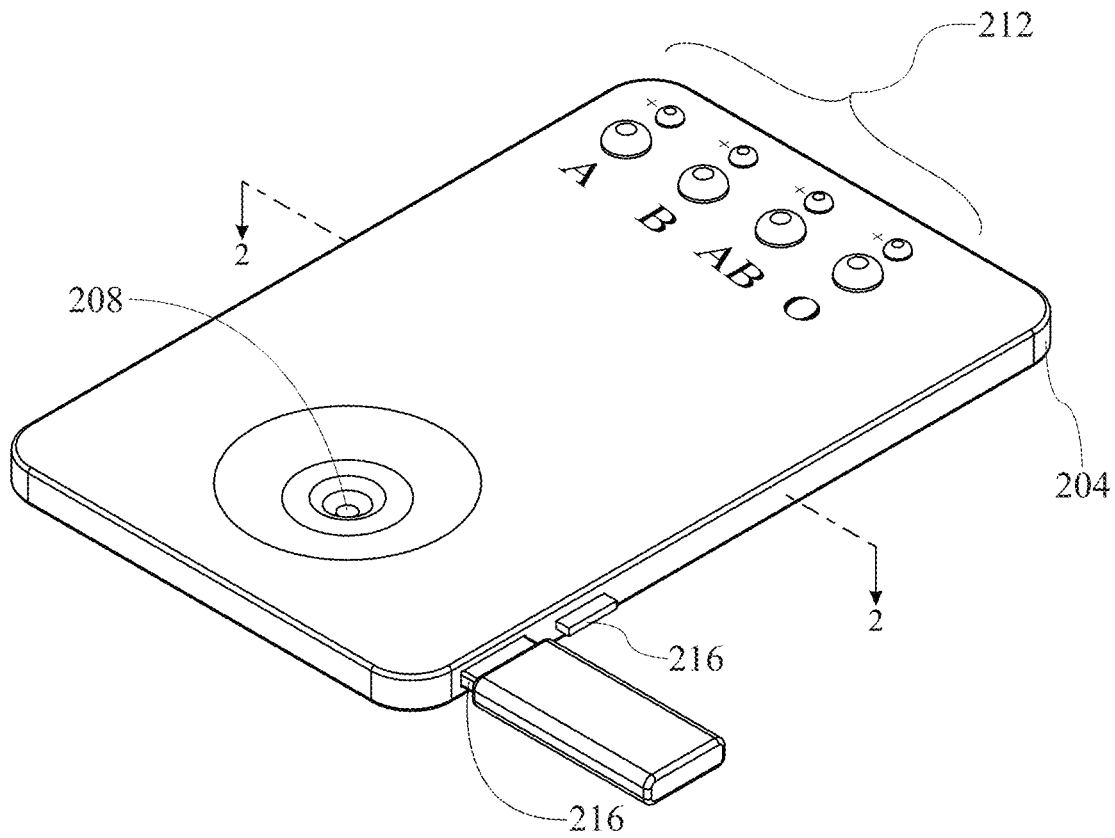
FIG. 6 presents a perspective view of an alternate embodiment of the blood typing device comprising a cassette-style housing with labeled visual output indicators corresponding to blood types A, B, AB, and O, and a circular sample application port located on a top surface, wherein a digital communication module is shown extended from a side of the housing.

Referring now to FIG. 6, a detailed logic table 172 is shown that further elaborates the signal output structure of the blood typing device 100. FIG. 6 presents a tabular arrangement mapping combinations of antigen reactions for A, B, and Rh(D) antigens to specific signal outputs labeled S1 156, S2 160, and S3 164 (from FIG. 5). Each signal output may correspond respectively to detection of the A antigen, B antigen, and Rh(D) antigen. Binary values "1" and "0" represent positive and negative antigen reactions respectively, with "0" indicating absence of a detectable antigen. The signal outputs may then be used to resolve the final ABO and RhD blood type classification based on logical association of binary outcomes. The logic structure supports efficient and accurate blood type determination by reducing biological testing to a binary decision-making process.

In addition to standard blood type classifications, FIG. 6 further maps specific unassigned functions to rare blood type conditions, such as the identification of Rh-null blood. In particular, the logic table defines that if signal S3 164 outputs "000," corresponding to a triple-negative result across all evaluated antigens, the sample may be classified as Rh-null, also known as Golden Blood. This detection pathway provides an important diagnostic extension beyond standard ABO and RhD categorization and may be used to identify individuals with extremely rare blood types. The mapping of all assigned and unassigned binary combinations ensures comprehensive diagnostic coverage and minimizes ambiguity in the final blood type determination. The use of a progressive binary decision structure across S1 156, S2 160, and S3 164 simplifies classification into a consistent and scalable framework. This logical extension provides the ability to identify both common and rare blood type profiles using the same binary output structure.

The detailed logic illustrated in FIG. 6 may be implemented within the blood typing device 100 using printed reference tables, mechanical selector mechanisms, or electronic microcontroller logic. In embodiments utilizing electronic signal processing, binary signals derived from test zones A 108, B 112, and an Rh(D) detection zone may be converted into corresponding outputs displayed on a screen or transmitted to an external device. Alternatively, a purely mechanical or manual interpretation using printed binary keys may be provided on the housing of the device 100 to allow untrained users to determine their blood type easily and accurately. Implementation of the FIG. 6 logic may be adapted for different environments, including resource-limited settings, mobile diagnostic platforms, or digitally connected healthcare systems. The binary architecture also facilitates potential integration into machine learning platforms for enhanced diagnostic validation. FIG. 6 thereby supports a broad range of potential implementation modes while maintaining the fundamental logical structure of the invention.

The blood typing device 100 may include a housing or body formed from a disposable substrate such as polymeric material. The substrate may define internal fluidic channels configured to direct the blood sample from the sample application area to the test zones. The internal channels may be treated to resist protein adhesion or hemolysis. A collection reservoir may be positioned downstream of the test zones to retain unused sample fluid or waste. The housing may be designed to prevent leakage, evaporation, or environmental contamination during testing. Optional venting or pressure regulation features may allow gas exchange or controlled sample movement through capillary action.

The sample application area 168 may comprise a porous membrane or hydrophilic film designed to wick whole blood from a finger prick or capillary tube. The sample volume may be in the range of 5 to 30 microliters. The membrane may be disposed over a spreading layer that promotes even distribution of the fluid across the width of the device 100. Additional layers may be used to filter cells, isolate plasma, or neutralize interfering substances. The application area may be user-accessible and marked with visual indicators to guide sample placement. A sample wick timer may be incorporated to indicate when the sample has fully entered the test zone system.

Reagents disposed in zones A 108, B 112, and D (not shown explicitly but described) may be dried antibodies immobilized onto cellulose pads, nitrocellulose membranes, or gel matrices. These reagents may be stored in a stabilized form and rehydrated upon contact with the applied sample. The anti-A and anti-B reagents may comprise monoclonal antibodies selected to detect the corresponding antigens with high specificity. In embodiments where RhD is detected, the anti-D reagent may comprise humanized monoclonal IgM or IgG antibodies. Stabilizers or preservatives may be incorporated to extend shelf life and enhance temperature resilience. Each reagent zone may also include contrast-enhancing dyes to improve the visibility of reactions.

Each reagent zone may be visually read by observing a change in color, precipitation, or opacity. Alternatively, the reaction may be evaluated through reflective or transmissive optical detection. An onboard indicator may be used to confirm that the reagents are functional and the sample volume was sufficient. Color scales or digital readers may be used to compare reaction intensity to standardized benchmarks. Color change thresholds may be printed on the housing or embedded in an app to assist with interpretation. Red-green-blue (RGB) or hue-saturation-value (HSV) scoring systems may be used to digitize the interpretation for further processing.

The output mechanism may be passive, such as printed visual guidance that maps the observed color change to a blood type result, or active, such as an LED array 172 (as shown in FIG. 2) driven by a logic controller that lights up the corresponding blood type designation. In some embodiments, a microcontroller may process the binary values from each test zone and generate a digital signal. This signal may be output to a display, saved to onboard memory, or transmitted wirelessly to a mobile device. The display may be an LCD, e-ink surface, or mechanical switchplate. Transmission protocols may include Bluetooth, near-field communication (NFC), or infrared. The device 100 may also be configured to work with health informatics systems, mobile apps, or cloud storage systems for automated recordkeeping.

In certain configurations, the device 100 may also include a QR code or alphanumeric code associated with each possible output. The determined code may be marked visibly on the housing or may be presented via a mechanical window that rotates or shifts in response to internal logic changes. The user may then scan or record the code for further use in a medical database or diagnostic report. Codes may represent a checksum or hash of the binary output to ensure traceability. Mechanical codes may be aligned with shifting panels or rotating disks activated by internal fluid or mechanical triggers. These components may be used in conjunction with visual output for users without access to digital infrastructure.

Control mechanisms such as region C 124 shown in FIG. 1 and FIG. 2 may contain reagents configured to indicate that the sample has properly flowed through the device 100 and that all test regions have been adequately hydrated. The control region C 124 may show a standard color when the test is functioning correctly and may remain blank or discolored if the device is compromised or expired. The control mechanism may validate sample sufficiency and reagent rehydration and may serve as a safeguard against interpreting partial or incomplete results. Control zones may include pH indicators, migration bars, or embedded timers.

This feature may be particularly useful in decentralized or unsupervised testing environments. Devices lacking a functional control region output may be flagged as invalid and discarded.

The layout of the antigen zones may be adjusted in alternative embodiments to accommodate different reagent loading strategies or manufacturing constraints. For example, the zones may be arranged radially, linearly, or in a matrix configuration depending on the format of the device 100. A circular or spiral layout may facilitate compactness and rotational reading mechanisms. Linear formats may be compatible with dipstick-style cassettes or roll-to-roll production. Matrix arrays may enable multiplexed testing for multiple antigens simultaneously. These format variations may offer flexibility across different markets or clinical contexts.

The test zones may be separated by physical barriers or hydrophobic regions to prevent cross-contamination. In embodiments where sample overflow is a concern, an absorbent pad may be disposed downstream of the zones to capture excess fluid. These fluid control mechanisms may ensure clean signal resolution and prevent erroneous interpretation. Materials such as polyethylene, silicone, or wax barriers may be used to guide or restrict fluid flow. Isolation zones may also act as buffers to improve accuracy. The absorbent zone may also aid in safe disposal of residual blood and reagents.

The device 100 may be configured for use in various settings such as disaster response, battlefield medicine, or remote clinical outreach. The lightweight and compact form factor may allow multiple units to be shipped and stored with minimal logistics. Packaging may include desiccants and temperature indicators to ensure viability under rugged conditions. Instructions for use may be printed on the casing or included as illustrated guides for low-literacy users. The device may be operable without external power or instruments. This ruggedized, autonomous format may address critical needs in underserved regions.

In some implementations, the device 100 may be manufactured in roll format, where multiple tests are arranged sequentially on a continuous tape. The tape may be cut or separated after each use. This configuration may be suited for high-volume environments or integrated testing workflows. The roll format may use perforations, adhesive sections, or tear-away flaps for convenience. Applications may include clinical laboratories, blood donation drives, or automated sorting systems. Printed identifiers or barcodes may track each test unit for traceability.

The invention may be further configured to detect additional antigens such as Kell, Duffy, or Kidd systems, by incorporating additional test zones and corresponding logic outputs. Each additional antigen may be assigned a binary output and processed within an expanded logic framework. The addition of more antigens may be modular or pre-integrated, depending on user needs. Kits may be customized for transfusion centers, prenatal clinics, or military deployments. Additional antigen detection zones may be color-coded for differentiation. Software or logic tables may be updated to reflect additional classification pathways.

Where desired, the test results may be digitized and processed by mobile applications. The device 100 may be photographed by a smartphone, and software may analyze the test zones for color or contrast differences. The binary outcome may then be displayed within the app and saved to a user profile or medical history. Image processing algorithms may correct for lighting, angle, or camera variability. Integration with electronic health records may be accomplished via secure file export. The app may also provide instructional guidance, test reminders, and interpretation validation.

In yet other embodiments, the device 100 may be configured to perform time-resolved reactions or include an electronic timer to indicate when to read results. This may be achieved by chemical delay layers or microfluidic timing channels. Delays may improve result contrast and prevent premature reading. Timers may be mechanical, chemical, or electronic. Visual countdown indicators may inform the user when the device is ready for reading. Such timing mechanisms may standardize use and reduce user-dependent variability.

All components of the device 100 may be formed from medically safe materials and may be configured to comply with applicable standards for in vitro diagnostics, sterility, and single-use biohazard disposal. Materials may include plastics, adhesives, membranes, and reagents validated for diagnostic accuracy. Disposal methods may follow guidelines for blood-contaminated waste. Packaging may support tamper-evidence and sterility assurance. The design may meet regulatory requirements from agencies such as the FDA or WHO. Sustainability features may be incorporated through biodegradable components or recyclable packaging.

The features shown in FIGS. 1 through 5, including test zones A 108 and B 112, composite region AB 116, control zone C 124, logic diagram 128, sample identifiers 132, binary reaction indicators 136, and logic elements L 152, S1 156, S2 160, and S3 164 may be applied in various combinations to support alternative implementations without departing from the scope of the invention described herein.

In an alternate embodiment of the present invention, illustrated in FIGS. 6 through 10, the blood typing system may be implemented in a cassette-style format with integrated fluidic, visual, and digital output components. This alternate embodiment may be particularly suited for field, point-of-care, or digitally connected diagnostic environments where portability, real-time feedback, and electronic health record integration are beneficial. While the primary embodiment provides a logic-based interpretation of colorimetric or passive outputs, the alternate embodiment augments the system with structural and electronic enhancements that facilitate both visual and machine-readable result communication. The device may be operable by minimally trained personnel, such as in military, rural, or emergency settings, while still generating standardized blood typing classifications compatible with laboratory-grade systems. The design leverages modular logic mapping, integrated visual signaling, and optional digital transmission to improve overall accuracy, usability, and clinical efficiency.

As shown in FIG. 6, the alternate blood typing device 200 may include a generally rectangular housing 204 formed from a rigid polymer or composite substrate. A circular sample application port 208 may be located on the top surface of the housing 204 and configured to receive a whole blood sample via pipette, drop, or integrated lancing accessory. Toward the upper half of the housing, a set of labeled visual output indicators 212 may be aligned beneath corresponding blood type labels, such as A, B, AB, and O, each of which may include Rh(D)-specific positive (+) and negative (−) designations. Each visual indicator 212 may be a light-emitting diode (LED), electromechanical flag, or transparent window beneath which a colorimetric reaction surface is visible. The housing may further incorporate a digital communication module 216 mounted within a slot along the side edge of the housing 204. The communication module 216 may be deployable or detachable and may house one or more data ports, microcontrollers, or memory storage units for secure result transmission or data capture.

Figure 7:
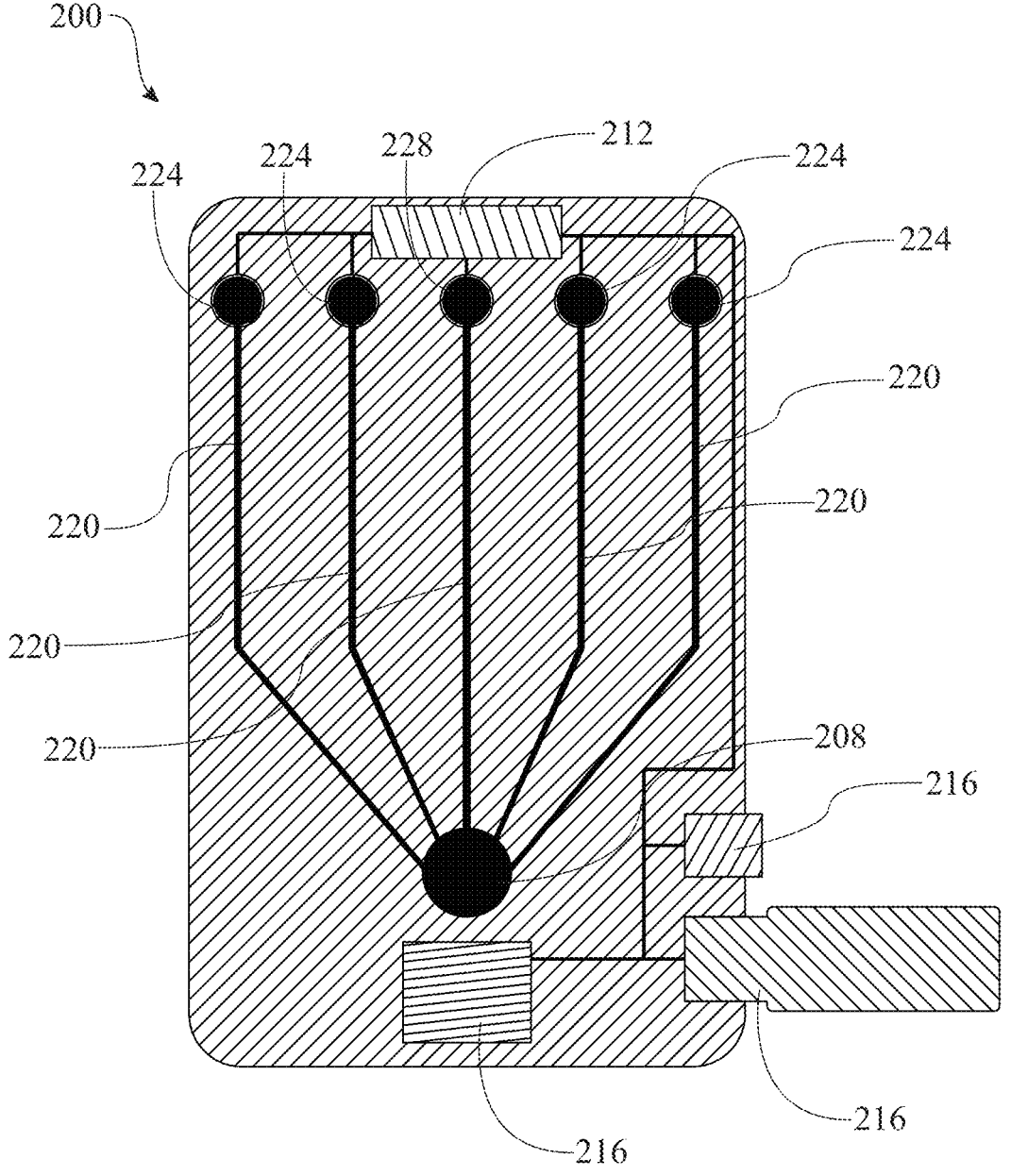
FIG. 7 presents a cross-sectional view of the alternate embodiment illustrated in FIG. 6, showing internal fluid pathways extending from a central sample application port to a plurality of reagent zones, with integrated components including a control region, result output elements, and a digital communication module extending laterally from the housing.

Referring to FIG. 7, the device 200 is shown in cross-section, illustrating the internal architecture that facilitates sample delivery and signal output. The sample port 208 may direct blood into a central fluidic junction connected to a branched microfluidic channel network 220. The microfluidic network 220 may distribute the sample uniformly to a series of reagent zones 224, each of which is preloaded with immobilized antibodies specific to antigens A, B, and D. Control region 228 may contain a control reagent designed to react regardless of antigen presence, thereby confirming proper sample flow and functional test operation. A waste containment chamber may be disposed downstream of the reagent zones 224 to receive excess fluid and prevent cross-contamination or leakage. Positioned adjacent to the fluidic system may be one or more electronic components operatively coupled to the communication module 216, allowing signal detection from the reagent zones and translation into digital binary output. Sensors in the zones may include optical detectors, resistive elements, or capacitive film layers capable of evaluating the presence and strength of agglutination or other reaction endpoints.

Figure 8:
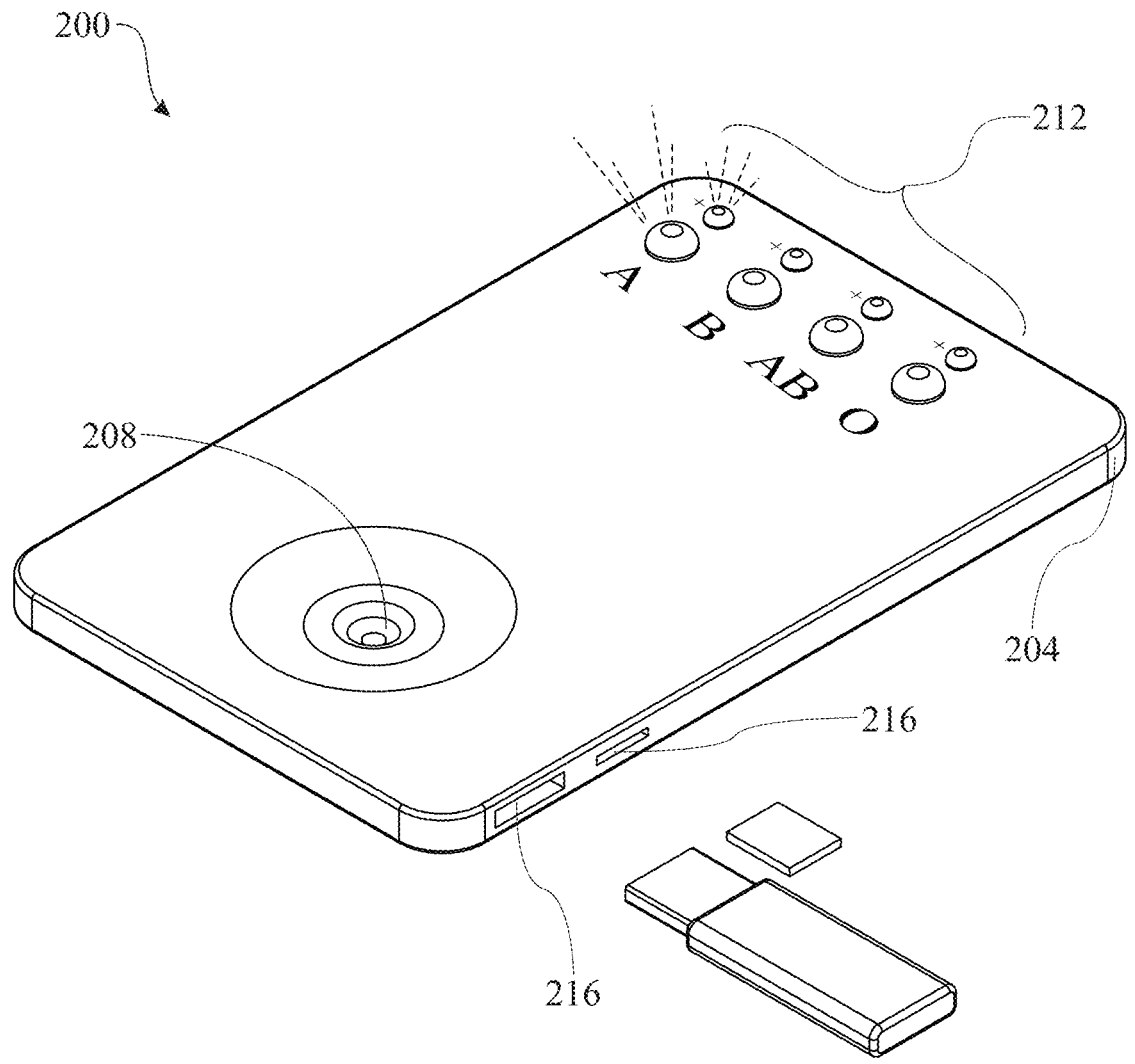
FIG. 8 presents a perspective view of the blood typing device shown in FIG. 6, illustrating a visual output condition in which one or more indicator lights are activated above the "A" zone, and further showing the communication module in a detached state with associated components positioned externally to the housing.

Turning to FIG. 8, the device 200 is shown during use, with the communication module 216 partially extended and one of the visual indicators 212 illuminated. In this example, the illuminated zone corresponds to the "A" designation, suggesting a detected agglutination in the anti-A reagent zone. Other indicators may remain unlit, indicating no reactivity. The indicators 212 may activate via sensor feedback signals processed through an embedded microcontroller, or via direct chemical-to-electrical transduction depending on implementation. The communication module 216 may be configured to output results in human-readable form on a display, or digitally encode results using HL7, FHIR, or custom XML structures for integration into electronic medical record (EMR) systems. A protective cap or shield may be included to cover the communication module 216 during storage or transport, preserving sterility and protecting contact points or antennas from damage.

FIG. 9 presents a tabular logic chart 240 illustrating the mapping of input binary values to corresponding blood type classifications. The chart 240 may reflect all permutations of reactivity in the A, B, and Rh(D) antigen zones, formatted as binary values where 1 indicates agglutination and 0 indicates no agglutination. Each row in the chart represents a unique output combination (e.g., A+, B−, AB+, O−), which may be cross-referenced against results detected by the system. This chart 240 may be printed on the back or side of the device housing, encoded within a mobile application interface, or embedded as a visual lookup guide beneath a transparent lid. In some implementations, the device may highlight the matching row in the chart automatically upon detecting a confirmed binary output. By using standardized binary mapping, the device promotes consistency in classification and simplifies interpretation across users and environments.

Figure 10:
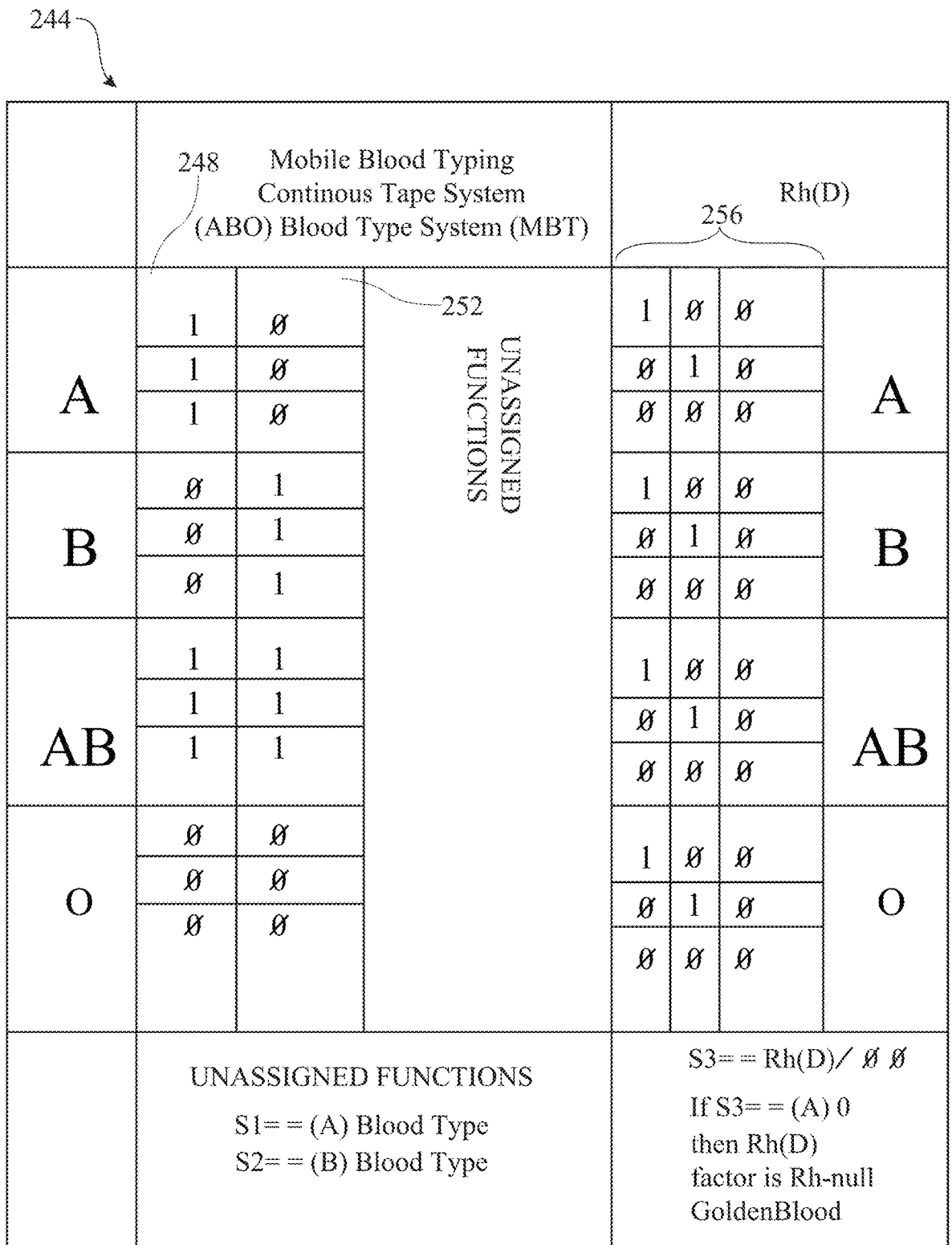
FIG. 10 presents an expanded logic table for a mobile blood typing system, showing combinations of binary input values corresponding to A, B, and Rh(D) antigen detection, and illustrating how signal outputs S1, S2, and S3 are used to determine ABO and Rh classification, including detection of Rh-null (Golden Blood) when all Rh(D) values are absent.

FIG. 10 illustrates a more comprehensive logic matrix 244 incorporating signal outputs S1 248, S2 252, and S3 256, which correspond to detection of the A antigen, B antigen, and Rh(D) antigen, respectively. The matrix 244 presents a structured mapping of each signal triplet to a resolved blood type classification. The binary states represented as 1 and 0 (or slashed zeroes) denote positive or negative reactions in each test zone. A detected signal triplet of (1, 0, 1) may resolve to A positive, while (0, 0, 0) may resolve to O negative. Notably, when signal S3 256 outputs a triple-zero state indicating absence of Rh(D) antigen detection across all validation criteria, the system may classify the result as Rh-null or Golden Blood. This classification may be displayed with special notation or flagged for clinical escalation. The matrix 244 may be referenced internally via a firmware-encoded truth table or used in mechanical implementations via printed overlays or analog decoding modules. The incorporation of S1-S3 logic into the physical and digital infrastructure of the device 200 enhances its diagnostic accuracy, scalability, and compatibility with both manual and automated workflows.

A method for determining a blood type using the device 100 may comprise the steps of applying a whole blood sample to the sample application area 168, distributing the sample to test zones A 108, B 112, and optionally to a RhD zone, initiating antigen-antibody reactions in the test zones, assigning a binary value to each test result based on presence or absence of agglutination, referencing a logical mapping structure configured to associate each binary combination with a blood type, and outputting the corresponding blood type visually or electronically. The method may begin with preparing the sample area, ensuring the sample is applied uniformly. Upon contact, reagents may react within a set duration, after which results may be reviewed. Each antigen test zone may yield a digital or colorimetric indicator. The binary results may be compiled in a lookup table. The final classification may be recorded, displayed, or transmitted.

In one aspect of the method, a control region C 124 may be used to validate test completion and sample sufficiency. In another aspect, a printed or electronic chart may be used to interpret the binary outputs. In still another aspect, the method may further comprise digitizing the result and transmitting it to an external computing device or server. The method may optionally include storing the result in a cloud database for clinical access. A timestamp and batch number may be encoded with the result for audit purposes. Quality control flags may be applied if inconsistencies are detected in the control region or test zones.

Alternate embodiments may include versions of the device 100 wherein the output mechanism comprises a mechanical display window configured to reveal a result code. Another alternate embodiment may feature a communication module that transmits test results via Bluetooth or NFC. Still further embodiments may utilize reflective or fluorescent markers in place of colorimetric indicators. The logic processing unit L 152 may be implemented as discrete logic circuitry, a microcontroller, or software executed by an embedded processor. Embodiments may support customization of reagent types, zone arrangements, and output modes. These variations enable the invention to adapt to different diagnostic needs and regulatory requirements.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A disposable blood typing device for determining an ABO and RhD blood type of a blood sample, the device comprising:
    (a) a housing comprising a plurality of test zones including:

(i) a first test zone containing an anti-A reagent configured to detect an A antigen in the blood sample,
        (ii) a second test zone containing an anti-B reagent configured to detect a B antigen in the blood sample, and
        (iii) a third test zone containing an anti-D reagent configured to detect a D antigen in the blood sample;
    (b) a sample application area in fluid communication with each of the plurality of test zones;
    (c) a binary output mechanism associated with each test zone and configured to display a binary signal or visual indicator comprising a first state corresponding to the presence of antigen and a second state corresponding to the absence of antigen; and
    (d) a logical mapping structure operatively associated with the binary output mechanism, the logic mapping structure comprising a truth table, logic chart, or equivalent circuit configured to:
        (i) receive the combination of binary outputs from the first, second, and third test zones; and
        (ii) classify the blood sample into a specific ABO and RhD blood type based on the combination of binary outputs according to a predefined logical mapping framework.

2. The device of claim 1, wherein the binary output mechanism comprises a colorimetric indicator configured to change color in response to an agglutination reaction in each respective test zone.

3. The device of claim 1, binary output mechanism comprises an electronic indicator selected from the group consisting of a light-emitting diode (LED), a digital display, and a visual signal on a screen.

4. The device of claim 3, wherein each test zone is operatively coupled to a corresponding LED that illuminates in a first color in response to the presence of antigen and in a second color in response to the absence of antigen.

5. The device of claim 1, wherein the logical mapping structure comprises a preconfigured Boolean logic circuit that receives the binary outputs from the test zones and generates an output signal corresponding to the determined blood type.

6. The device of claim 1, wherein the logical mapping structure comprises a printed chart or matrix printed on the housing that maps all possible binary combinations to corresponding blood type classifications.

7. The device of claim 1, further comprising a display area on the housing configured to visually present the determined blood type to a user based on the binary outputs of the test zones.

8. The device of claim 1, wherein each of the anti-A reagent, anti-B reagent, and anti-D reagent is provided in a dried, stabilized form within a gel or porous membrane.

9. The device of claim 1, wherein the sample application area is configured to receive a whole blood sample and direct the sample to the test zones via capillary action or microfluidic channels.

10. The device of claim 1, wherein the housing is formed as a single-use, sealed cassette configured to prevent re-use or cross-contamination.

11. The device of claim 1, further comprising a waste containment region within the housing configured to retain excess sample and reduce biological exposure risk.

12. The device of claim 1, wherein the logical mapping structure comprises an integrated circuit configured to convert the binary outputs into a machine-readable data format.

13. The device of claim 12, further comprising a communication module configured to transmit the machine-readable data format to an external device selected from the group consisting of a smartphone, a computer, and a remote server.

14. The device of claim 1, further comprising a control region comprising a control reagent configured to confirm that the sample has been properly introduced and that reagents are functional.

15. The device of claim 1, wherein the device further comprises a power source configured to energize one or more components of the result output mechanism or logical mapping structure.

16. The device of claim 1, wherein the result output mechanism comprises a mechanical window revealing a graphical symbol corresponding to the result of each test zone.

17. The device of claim 1, wherein the housing further comprises instructional markings indicating sample placement, test zone identification, and interpretation instructions.

18. The device of claim 1, wherein the logical mapping structure is configured to generate a unique output code representative of the blood type, wherein the output code is scannable or interpretable by an external reader device.

19. A disposable blood typing device for determining an ABO and RhD blood type of a blood sample, the device comprising:

(a) a sealed housing formed as a single-use cassette, the housing comprising a sample application area and a plurality of fluidically connected test zones;

(b) a first test zone containing a dried anti-A reagent configured to detect an A antigen in the blood sample;

(c) a second test zone containing a dried anti-B reagent configured to detect a B antigen in the blood sample;

(d) a third test zone containing a dried anti-D reagent configured to detect a D antigen in the blood sample;

(e) a binary output mechanism associated with each test zone, the binary output mechanism comprising colorimetric indicators configured to produce a first visual state indicating presence of antigen and a second visual state indicating absence of antigen;

(f) a logical mapping disposed on the housing, the logical mapping structure comprising printed binary logic chart that maps combinations of binary outputs from the test zones to corresponding ABO and RhD blood type classifications;

(g) a control region comprising a control reagent configured to indicate validity of the test by indicating proper sample introduction and reagent functionality; and (h) a waste containment region positioned downstream of the test zones and configured to collect excess sample material and prevent re-use or cross-contamination.

20. A method for determining an ABO and RhD blood type of a blood sample using a disposable blood typing device, the method comprising:

(a) providing a disposable blood typing device comprising:

(i) a sample application area, (ii) a first test zone comprising a dried anti-A reagent configured to an A antigen in the blood sample, (iii) a second test zone comprising a dried anti-B reagent configured to an B antigen in the blood sample, (iv) a third test zone comprising a dried anti-D reagent configured to an D antigen in the blood sample, and (v) a binary output mechanism associated with each test zone, the binary output mechanism comprising colorimetric indicators configured to produce a first visual state indicating presence of antigen and a second visual state indicating absence of antigen;

(b) applying a blood sample to the sample application area;

(c) allowing the blood sample to flow to each of the first, second, and third test zones;

(d) observing the result output mechanism at each test zone to determine whether agglutination has occurred;

(e) assigning a binary value to each test zone based on the observed visual state, wherein the first visual state corresponds to a first binary value and the second visual state corresponds to a second binary value;

(f) referencing a logical mapping structure comprising a predefined binary logic chart or truth table to determine a corresponding ABO and RhD blood type classification based on the combination of assigned binary values.

* * * * *